US005780233A

United States Patent [19]
Guo et al.

[11] Patent Number: 5,780,233
[45] Date of Patent: Jul. 14, 1998

[54] ARTIFICIAL MISMATCH HYBRIDIZATION

[75] Inventors: Zhen Guo; Lloyd M. Smith, both of Madison, Wis.

[73] Assignee: Wisconsin Alumni Research Foundation, Madison, Wis.

[21] Appl. No.: 659,605

[22] Filed: Jun. 6, 1996

[51] Int. Cl.$^6$ .............................. C12Q 1/68; C07H 21/04
[52] U.S. Cl. ...................... 435/6; 536/24.3; 536/24.33; 935/8; 935/77; 935/78
[58] Field of Search .................. 435/6, 91.2, 91.5; 935/77, 78; 536/23.1, 24.3, 24.33

[56] References Cited

PUBLICATIONS

Iitiä et al. Biotechniques 17(3):566–573 Sep. 1994.
Bergstrom, et al., "Synthesis, Structure, and Deoxyribonucleic Acid Sequencing with a Universal Nucleoside: 1–(2'–Deoxy–β–D–ribofuranosyl)–3–nitropyrrole." *J. Am. Chem. Soc.* vol. 17, No. 4: 1201–1209 (1995).
Breslauer, et al., "Predicting DNA duplex stability from the base sequence." *Proc. Natl. Acad. Sci. USA* vol. 83:3746–3750 (1986).
Conner, et al., "Detection of sickle cell β$^s$–globin allele by hybridization with synthetic oligonucleotides." *Proc. Natl. Acad. Sci. USA* vol. 80:278–282 (1983).
Doktycz, et al., "Optical Melting of 128 Octamer DNA Duplexes." *The Journal of Biological Chemistry* vol. 270:8439–8445 (1995).
Ebel et al., "Very Stable Mismatch Duplexes: Structural and Thermodynamic Studies on Tandem G•A Mismatches in DNA." *Biochemistry* 31:12083–12086(1992).
Ikuta, et al., "Dissociation kinetics of 19 base paired oligonucleotide–DNA duplexes containing different single mismatched base pairs." *Nucleic Acids Research* vol. 15:797–811 (1987).

Loakes, et al., "5–Nitroindole as an universal base analogue." *Nucleic Acids Research* vol. 22:4039–4043 (1994).
McGraw et al., "Sequence–Dependent Oligonucleotide–Target Duplex Stabilities: Rules from Empirical Studies with a Set of Twenty–Mers." *Bio Techniques* vol. 8:674–678 (1990).
Milburn, Sue, Ph.D., "Purify mRNA Rapidly with High Yield." *Ambion* vol. 3:1–12 (1996).
Nichols, et al., "A universal nucleoside for use at ambiguous sites in DNA primers." *Nature*, 369:492–493 (1994).
Wallace, et al., "The use of synthetic oligonucleotides as hybridization probes. II. Hybridization of oligonucleotides of mixed sequence to rabbit β–globin DNA." *Nucleic Acids Research* vol. 9:879–894 (1981).
Werntges, et al., "Mismatches in DNA double strands: thermodynamic parameters and their correlation to repair efficiencies." *Nucleic Acids Research*, vol. 14, No. 9:3773–3790 (1986).

*Primary Examiner*—Stephanie W. Zitomer
*Assistant Examiner*—Debra Shoemaker
*Attorney, Agent, or Firm*—Quarles & Brady

[57] ABSTRACT

An improved nucleic acid hybridization process is provided which employs a modified oligonucleotide and improves the ability to discriminate a control nucleic acid target from a variant nucleic acid target containing a sequence variation. The modified probe contains at least one artificial mismatch relative to the control nucleic acid target in addition to any mismatch(es) arising from the sequence variation. The invention has direct and advantageous application to numerous existing hybridization methods, including, applications that employ, for example, the Polymerase Chain Reaction, allele-specific nucleic acid sequencing methods, and diagnostic hybridization methods.

5 Claims, 8 Drawing Sheets

```
Probe(Perfect Match)   5'   CAGATCGGCTGAACTCCACA   3'
Probe(1 mismatch)      5'   --------A-----------   3'
Probe(2 mismatches)    5'   --------AA----------   3'
Probe(3 mismatches)    5'   -------TAA----------   3'
Target                 3'   GTCTAGCCGACTTGAGGTGT   5'
```

```
Probe:     5' CTCTTGAGAGAGCTAGTATCT 3'
           5' CTCTTGAZAGAGCZAGTATCT 3'
           5' CTCTTGZGAGAGCTZGTATCT 3'
           5' CTCTTZAGAGAGCTAZTATCT 3'
           5' CTCTZGAGAGAGCTAGZATCT 3'
           5' CTCZTGAGAGAGCTAGTZTCT 3'
Target:    3' GAGAACTCTCTCGATCATAGA 5'
```

ARTIFICIAL MISMATCH HYBRIDIZATION

STATEMENT REGARDING FEDERALLY SPONSORED RESEARCH OR DEVELOPMENT

This invention was made with United States Government support awarded by DOE Grant #: DE-FG02-91ER61122 and NIH Grant No. HG00321. The United States Government has certain rights in this invention.

FIELD OF THE INVENTION

The present invention relates to the field of molecular biology and more particularly to the field of nucleic acid hybridization.

BACKGROUND OF THE INVENTION

A standard method for detecting a variation in a nucleic acid sequence depends upon specific recognition by one oligonucleotide strand of a complementary nucleic acid target strand. When the probe and the target are not identical, the affinity of the two strands for one another is reduced. Reduced affinity is manifested by a decrease in duplex thermal stability which can be conveniently monitored by measuring the duplex melting temperature ($T_m$). The difference in duplex melting temperatures ($\Delta T_m$) between, on the one hand, a perfectly matched probe and target and, on the other hand, the same probe with a second target that differs from the first target at one nucleotide, has proven useful in detecting sequence variations in DNA. Wallace, B. R. et al., *Nucleic Acids Research* 9:879 (1981) discriminated between short oligomers differing at a single base. Subsequently, Conner, B. J. et al., *Proceedings of the National Academy of Sciences USA* 80:278 (1983) used the Wallace approach to investigate point mutations in the β-globin gene. The thermodynamics underlying this molecular discrimination have been further characterized by Ikuta, S. et al., *Nucleic Acids Research* 15:797 (1987), Doktycz, M. J. et al., *Journal Biological Chemistry* 270:8439 (1995), Breslauer, K. J., et al., *Proceedings of the National Academy of Sciences USA* 83:3746 (1986), McGraw, R. A., et al., *BioTechniques* 8:674–678 (1990). As a result, duplex thermal stability can be reasonably accurately predicted on the basis of sequence mismatches. The papers mentioned in this paragraph are specifically incorporated herein by reference.

Although hybridization can be a useful and powerful technique, it is limited in that the stability difference between a perfectly matched duplex and a mismatched duplex, particularly if the mismatch is only a single base, can be quite small, corresponding to a difference in $T_m$ between the two of as little as 0.5 degrees. See Tibanyenda, N. et al., *Eur. J. Biochem.* 139:19 (1984) and Ebel, S. et al., *Biochem.* 31:12083 (1992), both of which are incorporated herein by reference. More importantly, it is understood that as the length of the oligomeric probe increases, the effect of a single base mismatch on overall duplex stability decreases. This is an important limitation because it is desirable to increase probe length to enhance hybridization specificity for single genes while excluding weakly related genes. Thus, the ability to specifically distinguish closely related genes has not kept pace with the desire to focus hybridization studies on increasingly narrow regions of the genome. What is desired is a method that improves the ability to distinguish closely related genes by increasing the difference in melting temperatures of duplexes formed between probe and target.

A universal nucleoside analogue, 1-(2'-Deoxy-β-D-ribofuranosyl)-3-nitropyrrole, maximizes stacking interactions while minimizing hydrogen-bonding interactions without sterically disrupting a DNA duplex. This analogue is described in Nichols et al., "A universal nucleoside for use at ambiguous sites in DNA primers," *Nature* 369:492 (1994) and Bergstrom, D. E. et al., "Synthesis, Structure, and Deoxyribonucleic Acid Sequencing with a Universal Nucleoside: 1-(2'-Deoxy-β-D-ribofuranosyl)-3-nitropyrrole," *J.A.C.S.* 117:1201 (1995), both of which are incorporated herein by reference. The analogue can function as a "wild-card" in base pairing within nucleic acid duplexes.

SUMMARY OF THE INVENTION

The present invention is summarized in that an improved method for hybridizing an oligonucleotide probe to a nucleic acid target improves the ability to distinguish a first ("control") nucleic acid target from a second ("variant") nucleic acid target that differs from the control target.

Accordingly, the present invention is, in part, a hybridization method that employs a modified oligonucleotide probe that generally complements, but does not fully complement, a control nucleic acid target. The probe is not fully complementary to the control target in that the probe is modified at at least one position other than a position that is known to vary. The modification compels a non-complementary mismatch between the probe and the target.

When the probe is thus artificially modified at a single position, the probe and the control target will necessarily differ from each other at at least one position, while the probe and a target containing the sequence variation will necessarily differ from each other at at least two positions (one artificial mismatch and one true mismatch). It is herein demonstrated that a greater duplex thermal stability difference is observed between a duplex containing two mismatches and a duplex containing one mismatch (FIG. 1, Panel B) than is observed between duplexes containing one versus zero mismatches (FIG. 1, Panel A). Accordingly, the method offers improved ability to discriminate a variant target from a control target after a hybridization reaction. The invention is also a method for determining whether a nucleic acid target in a sample contains a sequence variation of interest.

In the method, the modified oligonucleotide probe is hybridized under suitable hybridization conditions to a nucleic acid target that may vary from the control target. A duplex that the probe forms with the variant target is less thermally stable, and has a lower melting temperature ($T_m$), than a duplex formed with the control target because it contains a true mismatch in addition to the artificial mismatch.

The $\Delta T_m$ between the two duplexes is appreciably larger than in previous comparisons between perfectly matched helices and helices mismatched only at the polymorphic position, thus facilitating discrimination of a control (or "normal") target from a variant target. The method of the present invention can be directly employed in many existing molecular biological applications, as is described in more detail elsewhere herein with the advantageous benefits of improved specificity and selectivity.

It is an object of the present invention to improve the ability to discriminate between nucleic acid targets containing or lacking a sequence variation.

It is a feature of the present invention that the oligonucleotide hybridization probe and the control target are not complementary to each other at at least one nucleotide position other than the position of the sequence variation.

It is another feature of the present invention that the additional non-complementarity of the probe reduces the stability and the $T_m$ of a duplex containing the probe.

It is an advantage of the present invention that a greater $\Delta T_m$ is observed between duplexes formed with (a) the modified probe and the control target and (b) the modified probe and the variant target than was observed in prior methods employing duplexes formed with (c) an unmodified probe and the control target and (d) the unmodified modified probe and the variant target.

It is another advantage of the present invention that the method offers greater selectivity and specificity in molecular biological processes.

Other objects, advantages and features of the present invention will become apparent upon consideration of the following detailed description taken in conjunction with the accompanying drawings.

BRIEF DESCRIPTION OF THE DRAWINGS

FIGS. 4A–C also depict the effect on $\Delta T_m$ of varying the position in the probe that corresponds to the true mismatch. Differences in melting temperature ($\Delta T_m$) between perfect match and 1-base mismatch hybridization (diamonds); and between 1-base artificial mismatch and 2-base (artificial plus true) mismatch hybridization (squares) are shown.

DETAILED DESCRIPTION OF THE INVENTION

Figure 1:
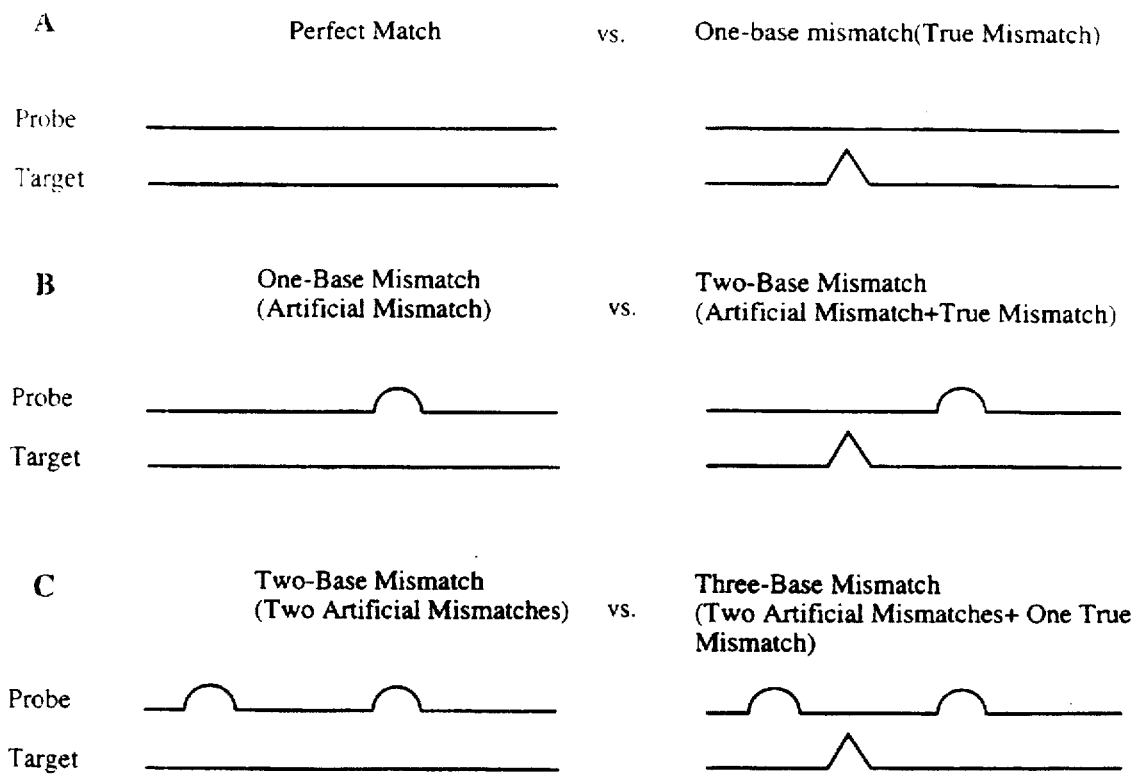
FIG. 1 A–C depicts and compares two embodiments of the artificial mismatch hybridization strategy with an existing strategy for detecting single nucleotide polymorphisms.

For purposes of this patent application, a "nucleic acid target" can be a chromosome or any portion thereof, or can be a recombinant nucleic acid molecule such as a plasmid, oligonucleotide, or other nucleic acid fragment, and may be naturally occurring or synthetic. The target length is not critical, provided that the target is sufficiently long to complement the modified probe, as described elsewhere herein. The nucleic acid target can be DNA or RNA. When the target is DNA, it is understood that the DNA is provided for use in the method in a denatured or single-stranded form capable of hybridizing to a single-stranded oligonucleotide probe.

Also in this application, a "sequence variation" or "variant" can include any change in a target sequence relative to a control or normal nucleic acid target. The difference can be as subtle as a single nucleotide polymorphism, but can also include two or more adjacent or non-adjacent single nucleotide changes, as well as more pronounced changes from the control that can include nucleic acid insertions, deletions, and rearrangements. Such insertions and deletions can be as small as 1 nucleotide, and no upper limit on insertion or deletion size is expected, if the oligonucleotide probe or primer is properly designed.

It will be appreciated that a target can be a "control" target only with reference to the different sequences of a "variant" target. For practical purposes, if a single target having clinical or laboratory significance in a particular assay is sought for analysis, that target should remain more stably paired to the oligonucleotide under the selected hybridization conditions (including, notably, salt, temperature, and pH conditions). The hybridization conditions should be such that a variant duplex having a lower thermal stability is destabilized relative to a control duplex because the variant duplex contains a true mismatch between the two strands in addition to the artificial mismatch.

Thus, if one desires to detect a particular nucleic acid target sequence or to use a particular sequence corresponding to the oligonucleotide in a subsequent method such as PCR or sequencing, one should designate the target containing that sequence as the "control target." For purposes of this application, a control target is defined as a nucleic acid target that more stably hybridizes with the selected primer or probe under the selected hybridization conditions.

Also in this patent application, "corresponding" nucleotides are nucleotides on opposite strands that would normally base pair with each other. A "mismatch" is found at any position where no direct Watson-Crick base pair (A/T, G/C, C/G, T/A) correspondence exists between the oligonucleotide and the target in the region of complementarity between the two strands. An artificial mismatch is typically provided at one or more single nucleotide positions in an oligonucleotide, but can include more extensive changes. A true mismatch in a duplex formed between an oligonucleotide and a variant target can include a substitution, an insertion, a deletion, and a rearrangement of oligonucleotide nucleic acid relative to the target. Substitution can be at one or more positions in the oligonucleotide.

In the three panels of FIG. 1 A–C, the upper strand of a schematic duplex represents an oligonucleotide probe that will or will not form an artificial mismatch in keeping with the present invention. The lower strand represents a target sequence that is either normal (left side) or variant at a single nucleotide position (right side). In each panel, the pointed mismatch represents a true mismatch, while the rounded symbol represents an artificial mismatch.

Panel A represents a conventional allele-specific oligonucleotide hybridization which compares the thermal stability of a perfectly matched duplex and a duplex containing one true mismatch. Panel B represents the artificial mismatch hybridization strategy of the present invention wherein the oligonucleotide probe includes a purposely introduced single artificial mismatch such that the differential in duplex thermal stability is determined between a one-base mismatch duplex and a two-base mismatch duplex. Panel C shows a second embodiment of the artificial mismatch hybridization strategy wherein more than one artificial mismatch can be introduced into the probe. When the probe contains two positions that will form artificial mismatches, differential duplex thermal stability is determined between a two-base mismatch and a three-base mismatch. Hybridizations can be performed under standard conditions known to the art for binding probes to targets. Conditions used in the Example are suitable, but it is understood that variations in salt, temperature, and pH can affect the hybridization strength and the thermal stability of any duplex formed. One of ordinary skill can modify the hybridization conditions to optimize the present invention for a particular probe and target, and for a particular application, as desired, in accordance with existing application protocols. Primers or probe sequences and hybridization conditions should be determined in accordance with the art-recognized understanding of the factors that affect duplex stability in various hybridization techniques.

The inventors have determined that it can be easier to distinguish a duplex containing n mismatches from a duplex containing n-1 mismatches (FIG. 1, panels B and C) than it is to distinguish a duplex containing one mismatch from a perfectly matched duplex (FIG. 1, panel A), where n is two or more, and can range as high as 7 or even higher. In the method of the present invention, the $\Delta T_m$ between such duplexes is generally between 1 C.° and 25 C.°, but can be greater or less. For better discrimination, the difference is preferably between 5 C.° and 25 C.°, is more preferably between 10 C.° and 25 C.°, and is most preferably between 15 C° and 25 C.°.

As a preliminary demonstration of this principal, the $T_m$s of 20-mer duplexes containing 0, 1, 2, or 3 adjacent mismatches were determined by standard methods. The probe and target sequences are shown beneath the plot in FIG. 2.

In all tests shown in FIGS. 2-5, absorbance was measured at 260 nanometers on a Hewlett Packard 8452A UV spectrometer equipped with an HP89090A Peltier block. A temperature ramp rate of 1° C. per minute was used. All measurements were made in 1.0M NaCl, 0.1 mM EDTA, 10 mM sodium phosphate, pH 7.0, at a strand concentration of 50 µM. All melting temperatures were determined in triplicate and varied by less than 0.4 degrees. Melting curves showing absorbance versus temperature were plotted and the average $T_m$ of each duplex was determined.

Figure 2:
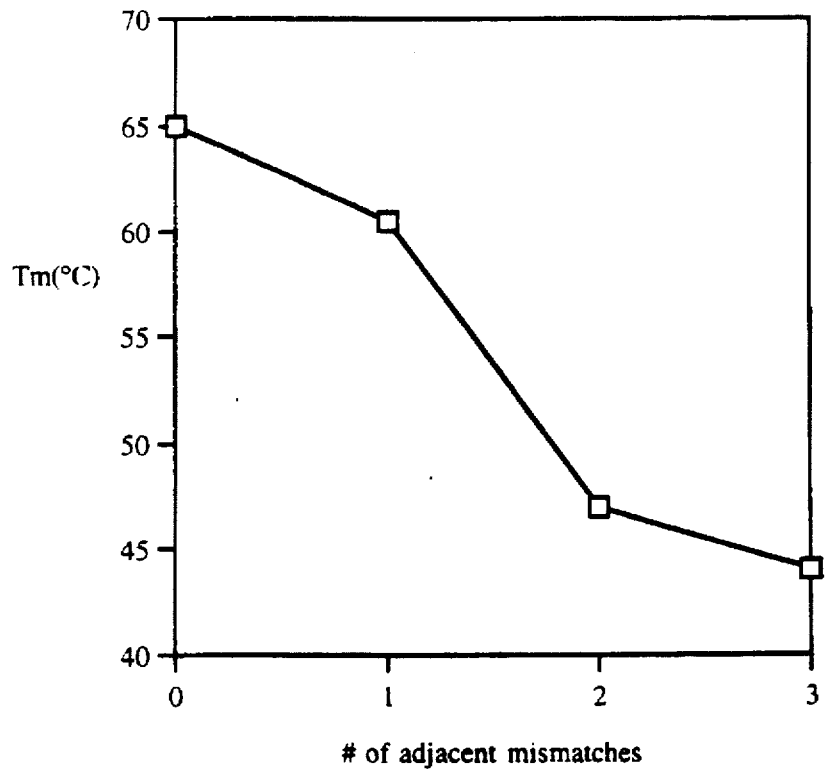
FIG. 2 compares the melting temperature of duplexes containing a target sequence and a probe having 0, 1, 2, or 3 mismatched bases.

The data of FIG. 2 were obtained using the natural mismatched bases shown below the plot. FIG. 2 shows a greater melting temperature differential ($\Delta T_m$) for one mismatch versus two mismatches ($\Delta T_m$=60° C.–47° C.=13 C.°) than for the standard perfect match versus one mismatch ($\Delta T_m$=65° C.–61° C.=4 C.°). It is appreciated that among mismatched natural bases, some residual interaction can exist (see Werntges, H. et al., Nucleic Acids Research 14:3773 (1986)). The extent of interaction can vary depending upon the particular combination of mismatched bases. In addition, duplex thermal stability can be affected by other variables that include the nature and position of the mismatches in the probes, as well as the sequence context of the mismatches and the probe length.

To eliminate effects caused by the nature of the mismatch itself, it is preferred that the nucleotide that will form the artificial mismatch with the target be a non-natural nucleotide residue in the probe. For simplicity, reference is made to the artificial or true "mismatch" in the probe, with the understanding that mismatches actually occur only when the modified probe is paired with a target.

It is preferred that the artificial mismatch bind poorly to the four naturally occurring nucleotides A, C, G, and T, so that no preferential stability effect is realized merely by introduction of the artificial mismatch. Suitable natural or non-natural artificial mismatches are, therefore, preferably universal mismatches. Such a universal mismatch could be a naturally occurring modified nucleotide or a non-natural nucleotide. A suitable artificial mismatch, when incorporated into an oligonucleotide probe, should form a reasonably stable duplex, preferably having a $T_m$ in the range of 25°–80° C. A non-naturally occurring nucleotide, 1-(2'-Deoxy-β-D-ribofuranosyl)-3-nitropyrrole (also referred to as "3-nitropyrrole 2'deoxyribonucleotide" or "3-nitropyrrole") has been identified by Nichols et al., supra, as being a suitable universal nucleotide for use at ambiguous sites in DNA primers. This nucleotide was shown to maximize stacking interactions while not disrupting duplex formation. These same attributes make this molecule a desirable universal mismatch nucleotide for use in artificial mismatch hybridization probes. For short probe lengths, however, a duplex containing a 3-nitropyrrole artificial mismatch may be too unstable to form under normal room temperature hybridization conditions. Such dramatic destabilization can be overcome by increasing the oligonucleotide length, which will necessarily produce a probe or primer having greater specificity. Thus, the destabilization that would otherwise have been a detriment to the method, can actually work to the great advantage of the user. By preparing a probe of suitable length, one can balance the desire for high specificity with a desire to carry out a reaction at a convenient hybridization temperature. Thus, improved discrimination can be achieved even in cases where the introduction of an artificial mismatch would initially appear to preclude duplex formation.

In view of this disclosure, one of ordinary skill will possess sufficient information to design a suitable probe or primer appropriate for a given application and having the advantages of the present invention. In addition, commercially available computer programs can assist in determining a suitable oligonucleotide sequence as well as suitable hybridization conditions for a reaction employing such an oligonucleotide. Since the art recognizes that it is not possible to completely predict the behavior of probes and targets in a hybridization reaction under defined conditions, empirical testing of proposed oligonucleotides and conditions are known by those having skill in the art to be an aspect of probe or primer design and such testing, therefore, would not be considered undue experimentation. Incorporation of an artificial mismatch should not otherwise affect the requirements of a probe or primer, although it may be desirable to adjust the hybridization conditions to improve discrimination, as is noted herein.

Other nitro- and cyano- substituted pyrrole deoxyribonucleotides could have similar strong stacking properties that could lessen the role of hydrogen bonding in base-pairing specificity. It may be desirable, in certain cases to seek out other universal base analogs which provide higher duplex stability, such as the 5-nitroindole derivatives described by Loakes, D. and D. M. Brown, Nucleic Acids Research 22:4039 (1994), incorporated herein by reference. Alternatively, other nitro- or cyano- substituted indoles might also be suitable artificial mismatch nucleotides. Also, an abasic nucleotide residue might be suitable. Unless otherwise noted, all subsequent work described in this application employed 3-nitropyrrole.

Hereinafter, guidance is provided as to the effect of other variables upon duplex stability in artificial mismatch hybridization. Further guidance is also provided in Nichols et al., supra, and Bergstrom et al., supra, both of which are incorporated herein by reference, concerning the considerable extent to which the universal analogue can be incorporated into a suitable probe.

Effect of Mismatch Position

Figure 3:
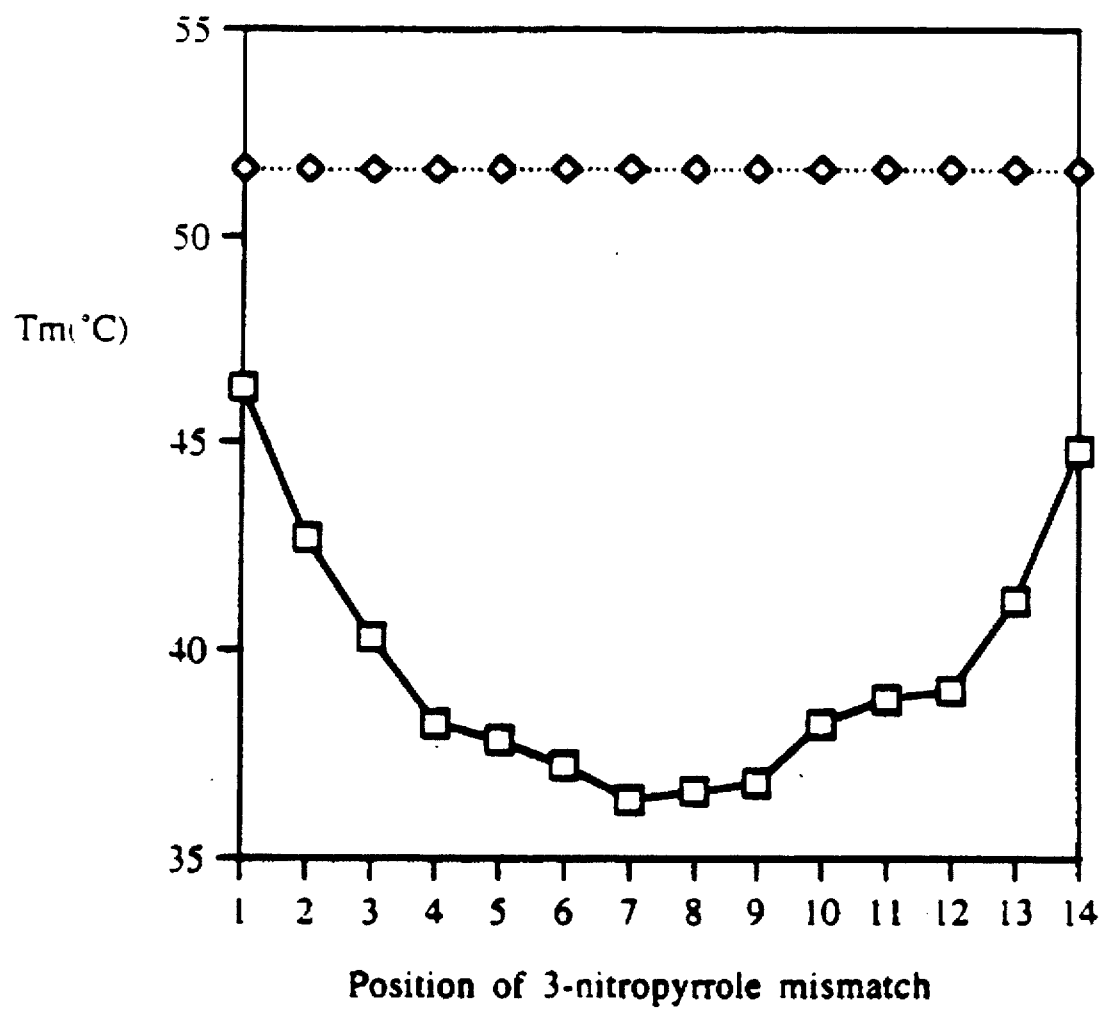
FIG. 3 compares the melting temperatures of duplexes containing a target sequence and a probe having one artificial mismatch at various positions along its length (squares). Also shown is the melting temperature of a duplex containing the same target sequence and a perfectly matched probe (diamonds).

FIG. 3 shows that duplex thermal stability varies depending upon the position of a single 3-nitropyrrole mismatch in a probe. The $T_m$ of a stable duplex between a target sequence (5'-AGATACTTCTATAACCAAGAG-3'(SEQ ID NO: 5)) and a probe fully complementary along its entire 15-base length is about 52° C. under the conditions employed. When an artificial mismatch is at or near the center of the oligonucleotide probe, the probe/target duplex is maximally destabilized (e.g., $T_m$ decreased 15°–17° C. relative to perfect match when mismatch was between the fifth and ninth positions of the probe). When the artificial mismatch is closer to either end, the duplex is destabilized to a lesser degree (e.g., $T_m$ decreased 60° C. or 70° C. relative to perfect match when mismatch was in the terminal nucleotide of the probe).

Effect of Distance Between True and Artificial Mismatches

Figure 4A:
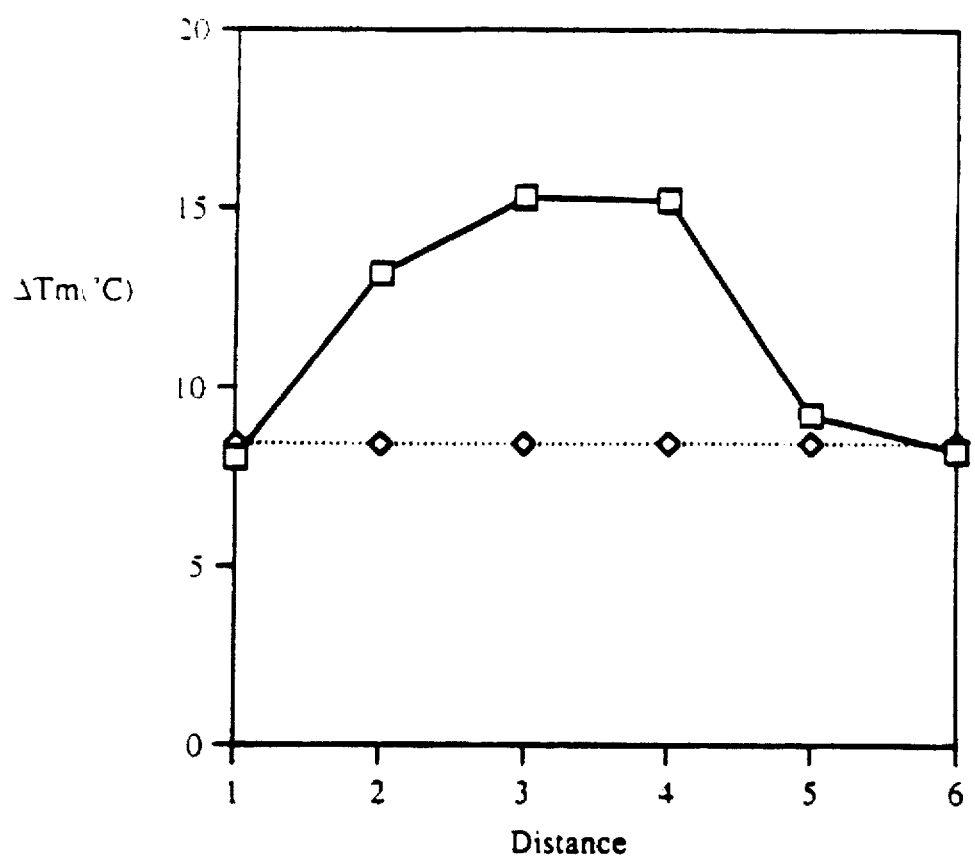
FIGS. 4A–C compares the effect of distance between a true mismatch on the target and an artificial mismatch on the probe.
Figure 4A:
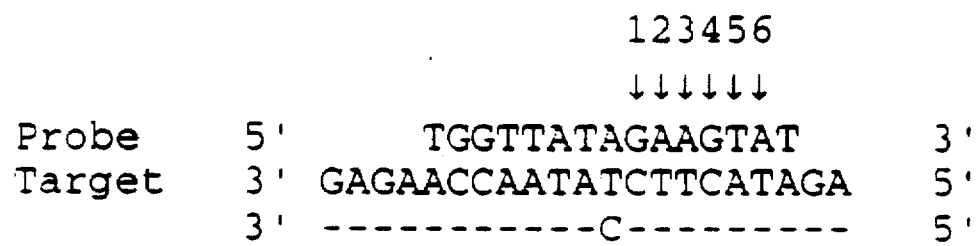
Figure 4B:
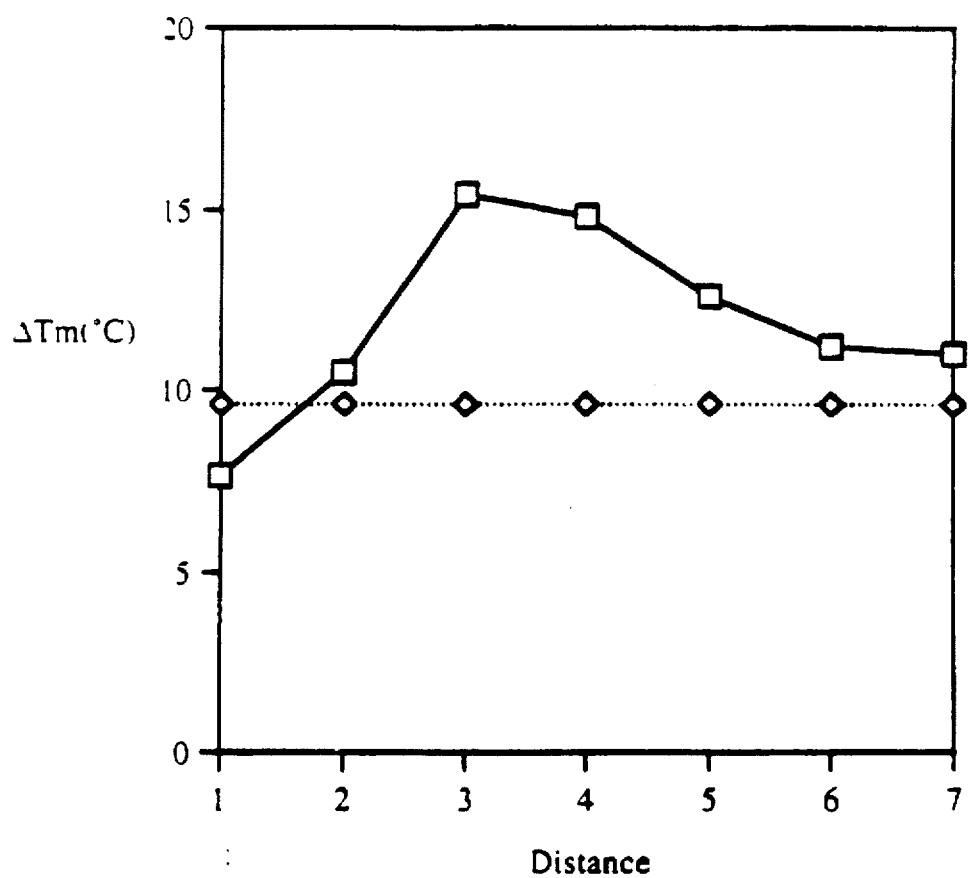
Figure 4B:
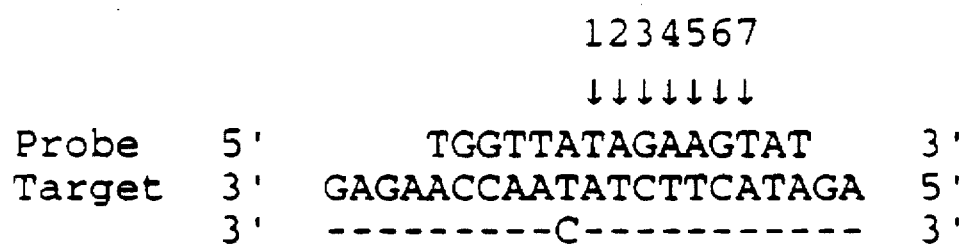
Figure 4C:
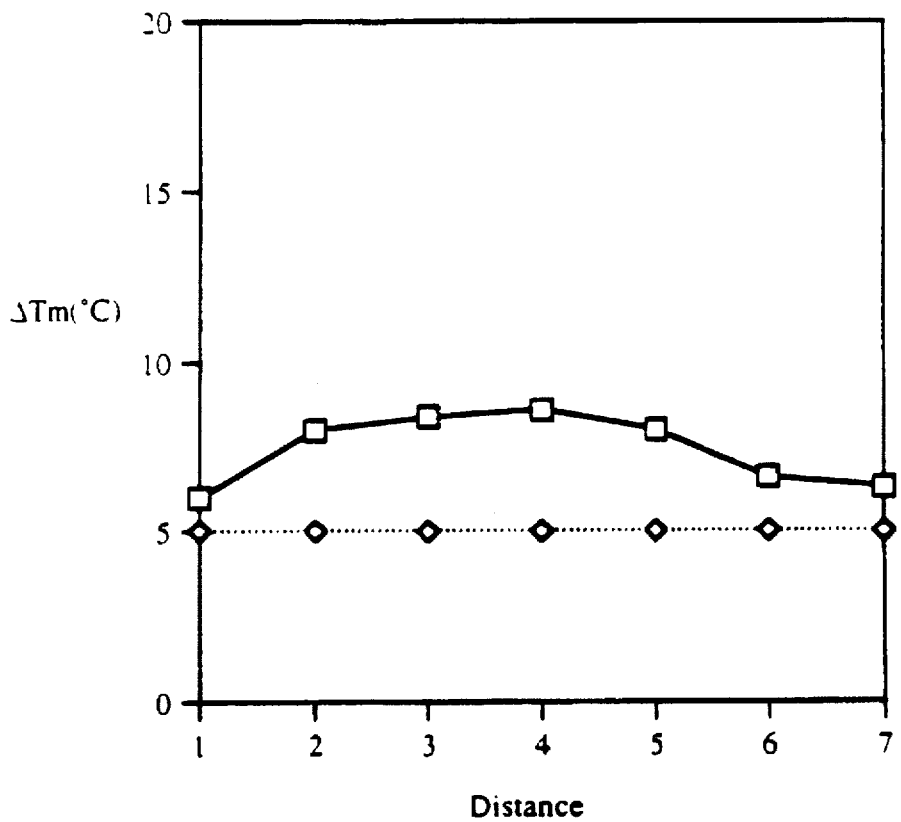
Figure 4C:
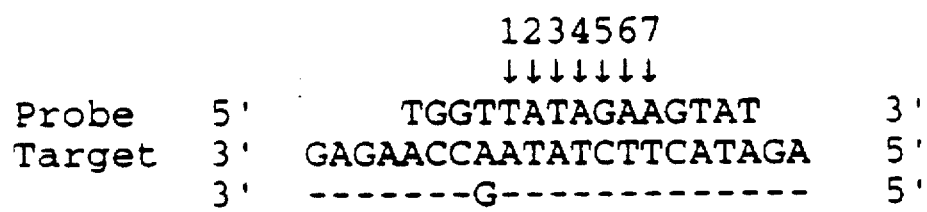

In FIGS. 4A–C, a 3-nitropyrrole nucleotide was systematically introduced into a position in the probe 1 to 6 bases away from a true mismatch. The true mismatch position was varied to correspond to position 8, 6, or 4 of a 15-mer oligonucleotide probe (FIG. 4A, 4B, 4C, respectively). The control target, the variant target, and the six probe variants for each case are shown beneath each plot. For comparison, FIGS. 4A–C also show the $\Delta_T m$ between duplexes containing 1 and 0 mismatches (as in FIG. 1, panel A), which are generally smaller than the $\Delta T_m$ in duplexes involving artificial mismatches.

The greatest $\Delta T_m$ is observed when a single artificial mismatch is introduced three or four bases away from the true mismatch, without regard to whether the true mismatch was situated at position 8, 6, or 4 of the 15-mer probe.

FIGS. 4A–C directly illustrate that the artificial mismatch hybridization method provides superior discrimination of single nucleotide polymorphisms than standard hybridization methods because a greater difference in duplex thermal stability is observed than in standard hybridization methods. In addition, this series of results demonstrates that the effect of the artificial mismatch upon hybridization stability depends strongly upon the relative position of the true and artificial mismatches, with the greatest destabilization consistently occurring when three to four bases separate the two. At such optimum spacing, the $\Delta T_m$s are increased by 3 C.° to 8 C.°, corresponding in each case to about a 50% discrimination gain.

FIGS. 4A–C, taken together, also demonstrate that as the true mismatch is closer to an end of the probe, the maximum differential melting temperature decreases from about 15 C.° or 16 C.° to less than 10 C.°, thereby reducing somewhat the enhancement afforded by the present method. This observation corresponds to that shown in FIG. 2, and suggests a preference for using a probe wherein the true mismatch corresponds to the center, or near center, of the probe. In each case, however, improvement is still observed over prior methods.

Similar experiments were conducted using natural unmodified base mismatches, however mixed results were obtained. In some cases, adding a second mismatch dramatically destabilized the duplexes, and the $\Delta T_m$ between a two base mismatch and a one base mismatch (FIG. 1, Panel B) was much greater than the $\Delta T_m$ between a one base mismatch and a perfectly matched duplex (FIG. 1, Panel A). In other cases, however, adding the second mismatch just slightly destabilized the duplex and virtually no difference in $T_m$ was observed. In contrast to the ambiguities inherent in natural base mismatches, the use of a non-naturally occurring base in the probe consistently enhanced the ability to discriminate single-base changes.

Effect of Providing and Positioning More Than One Artificial Mismatch

When the probe contained more than one artificial mismatch, enhanced discrimination was always observed relative to the conventional method. The enhancement was observed no matter where the mismatches were introduced, although a clear preference was observed for separating the mismatches so that they are separated by one complete helical turn, and hence are in relatively close proximity to one another. A 10 base separation between artificial mismatch positions is preferred. The dramatic decrease in thermostability observed at this spacing distance suggests a physical or chemical interaction between the mismatch groups.

Figure 5:
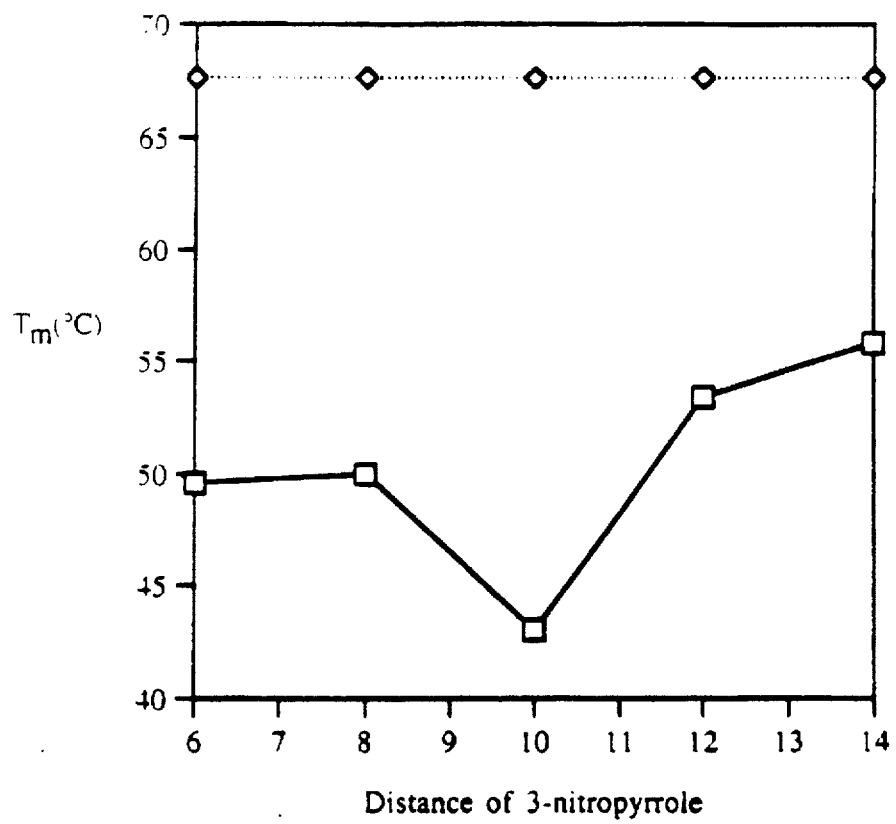
FIG. 5 shows the effect on $T_m$ of varying the distance between artificial mismatches on a probe containing more than one such mismatch. The melting temperatures for 21-mer duplexes containing two 3-nitropyrrole nucleosides on the probe strand (squares) were compared with the melting temperature for a perfectly matched duplex (diamonds). Z in the probe sequence indicates a 3-nitropyrrole nucleoside.

For example, FIG. 5 shows that the $T_m$ drops abruptly to the lowest point (about 44° C.) when two 3-nitropyrrole nucleotides positioned symmetrically about the center of a 21-mer oligonucleotide are separated by ten bases. At greater separations, the $T_m$ increases slowly with increasing separation. The $T_m$ of duplexes formed between the target and a probe containing the various pairs of artificial mismatches shown in FIG. 5 ranged from about 56° C. to about 440° C., depending upon the distance between the mismatched residues. Presumably, somewhat lesser, but still significant, effects would be observed if the mismatches were closer to one end of the probe, as has been shown for a single mismatch, supra. FIGS. 3 and 4A–C. For comparison, FIG. 5 shows a $T_m$ of about 68° C. for a duplex formed with the indicated 21 base long target and a probe perfectly matched to the target.

Table 1 reports the differential melting temperatures observed in conventional hybridization and artificial mismatch hybridization when probes contained two 3-nitropyrrole nucleotides. "Z" represents a 3-nitropyrrole in the indicated position. The polymorphic base in each target is underlined.

TABLE 1

| Distance Between 3-nitro-pyrrole | Probe Sequence SEQ ID No: 6 | $\Delta T_m$ (C.°) Target A* | Target B* |
|---|---|---|---|
| N/A | 5' CTCTTGAGAGAGCTAGTATCT 3' | 2.0 | 2.2 |
| 8 | 5' CTCTTGZGAGAGCTZGTATCT 3' | 3.3 | 3.8 |
| 10 | 5' CTCTTZAGAGAGCTAZTATCT 3' | 6.4 | 7.4 |
| 12 | 5' CTCTZGAGAGAGCTAGZATCT 3' | 3.1 | 3.9 |

*TARGET A: (SEQ ID No: 11) AGATACTAGCGCTCTCAAGAG
*TARGET B: (SEQ ID No: 10) AGATACTAGCTCGCTCAAGAG
PERFECTLY MATCHED TARGET: (SEQ ID No: 12) AGATACTAGCTCTCTCAAGAG

Shown in the first row of Table 1 are the $\Delta T_m$s comparing a perfectly matched duplex to a single-base mismatch duplex, where, in both cases, the probe had no artificial mismatch. In the perfectly matched duplex, the target was fully complementary to the probe. In the single-base mismatch duplexes, the target was either polymorphic target A or B.

The following rows of Table 1 show $\Delta T_m$s for two-base versus three-base mismatch, as was diagrammed in FIG. 1C, again using both polymorphic targets A and B. The various probes are shown in Table 1. When the artificial mismatches are separated by either eight or twelve bases, the $\Delta T_m$ increases by approximately 50%, which is similar to the results obtained for a single artificial mismatch. Interestingly, when the spacing between the artificial mismatches is ten bases, corresponding as above to approximately one complete helical turn, the $\Delta T_m$ dramatically increases to approximately 3-fold greater than that obtained for the conventional single-base mismatch. The abrupt increase in the ability to discriminate between duplexes at a spacing of ten nucleotides correlates with the drop in stability observed at the same spacing, as was shown in FIG. 5.

This result suggests that by incorporating additional artificial mismatches into a probe sequence, it will be possible to lengthen the overall probe length, thereby further improving the probe sequence specificity and the ability to distinguish between closely related DNA sequences in complex backgrounds.

The data presented herein suggest that a spacing of 10 nucleotides between artificial mismatches is desired. In addition, it will be appreciated that smaller separations are also effective within the method. An acceptable increase in $\Delta T_m$ has been demonstrated with a separation of 8 bases, and it is thought similar results will be observed with separation as low as 4 bases.

In view of the further recognition that a duplex containing too many mismatches is too unstable to form at room temperature, it is preferred by the inventors that artificial mismatch positions account for no more than about 20% of the total number of positions in a probe modified for use in the present invention. More preferably, no more than about 15% of the positions in the probe should be artificial mismatches. Most preferably, no more than about 10% of the positions in the probe should be artificial mismatches.

It will also be appreciated that the art is well aware of issues relating to probe length and hybridization. The present invention can be applied to oligonucleotides of any length acceptable to the art. The oligonucleotide need not correspond to the full length of the target. Likewise, the oligonucleotide can include sequences other than the portion that is generally complementary to the target. Oligonucleotide length is limited only by the ability to synthesize oligonucleotides. Using current technology, synthetic oligonucleotides in the range of about 100–150 nucleotides are readily made. Longer synthetic nucleotides of up to about 200 bases are now more difficult to prepare. It is anticipated, however, that as this developing field matures, it will become easier to synthesize oligonucleotides of 200 bases or more. More typically, oligonucleotides of about 50 bases are conveniently synthesized and used, and that is a preferred length. However, oligonucleotides can also be less than about 50 bases, more preferably less than about 40 bases, and still more preferably less than about 25 bases. Recognizing that specificity for a particular polymorphic locus increases with increasing probe length, the complementary portion of the probe should preferably be at least 10 bases long if a moderate level of specificity is desired.

A washing step to destabilize the variant duplex can be, but need not be, performed in connection with the invention. It may be desirable to completely eliminate the less stable duplex, however, this may not be essential; it may only be necessary to preferentially disrupt the less stable duplex. Alternatively, it may be desirable to disrupt some, but not all, of the more stable duplex in addition to the less stable duplex. Detection methods, including surface-sensitive methods, that can discriminate between the presence and absence of a duplex may be employed. Detection methods that do not require a wash step after hybridization include surface plasmon resonance and evanescent wave fluorescence detection.

Artificial mismatch hybridization increases the ability to discriminate normal sequences from point mutants. The ability to discriminate single nucleotide polymorphisms in the HLA-DRB locus illustrates the utility of artificial mismatch hybridization to increase the specificity of, for example, tissue typing, DNA diagnostic tests, genetic identity tests, allele-specific PCR, and sequencing by hybridization, by applying the principles of the invention to existing methods.

Having demonstrated the concept of the invention and its ability to detect subtle single nucleotide changes, as well as additional more complex differences between targets, the present inventors also note the general applicability of the invention to other techniques that employ nucleic acid hybridization in ways other than diagnostic indicators of a particular sequence variation.

Allele-specific PCR and allele-specific DNA sequencing, both of which are existing techniques that have been limited by insufficient ability to discriminate between alleles, are non-limiting examples of such uses. In either case, by selecting primers that complement one strand but not the other, then providing an artificial mismatch in the oligonucleotide primer, and selecting suitable hybridization conditions (e.g., temperature, pH, and salt), it is possible to ensure that stable duplexes form between the oligonucleotide and one allele but not between the oligonucleotide and the other allele. After forming the stable duplex, the amplification or sequencing reactions thus primed can then proceed according to existing protocols, with the advantage of selectively amplifying (using, e.g., PCR or another amplification method) or chain-extension sequencing (using, e.g., a DNA polymerase for primer extension) of a single allele.

Likewise, the general hybridization method disclosed herein is applicable to selective detection of individual genetic sequences in complex mixtures of sequences. For example, it is envisioned that a profile of viral genomes in a sample can be accomplished by sequentially or concurrently probing a DNA sample using a set of probes specific for particular viruses, where the probes contain artificial mismatches to improve the detection specificity. Similarly, the method enables the selective detection of heterozygotes where the alleles can be distinguished by careful design of a probe.

A stable duplex formed in the hybridization method of the present invention can be detected by any available methods or means. For example, detection can be realized by monitoring the subsequent production of a PCR-amplified fragment, or by tagging the oligonucleotide and monitoring for its presence, or by the surface-sensitive methods noted above. This list of detection strategies is not intended to be exhaustive. Rather, detection of a duplex formed in the present improved hybridization method can be accomplished using any method or means used in any existing application that includes a hybridization step. The utility of the process does not necessarily depend upon a desire to detect the more stable duplex formed in the reaction. It is contemplated that both duplexes can be detected in the same hybridization monitoring the stability difference between the two, for example, by monitoring the binding or disruption kinetics in the reaction. It is further specifically contemplated that a detection strategy can be employed in an automated system that can provide, for example, visual, auditory, or other sensory confirmation of duplex formation.

The applicants now present a non-limiting example of an assay in which the hybridization method of the present invention is used as a diagnostic tool to distinguish between complex related loci in the highly polymorphic HLA-DRB locus.

EXAMPLE

Discriminating among single nucleotide polymorphisms in HLA-DRB

The nucleotide sequence of the human HLA-DRB region is known and has been shown to contain many polymorphic sites, some of which are difficult to discriminate from one another by conventional hybridization.

Three distinct regions of the locus defined by amplification using PCR primers were employed as target sequences. The genotypes of the PCR products are DRB1*0301, DRB1*1101 and DRB1*1301, which were described by Bodmer, J. et al., Tissue Antigens 39:161 (1992), incorporated herein by reference. The three amplified portions are each about 260 nucleotides long.

Six oligonucleotide probes of sequences either perfectly complementary to the DNA targets or mismatched at one or two adjacent bases were immobilized on glass supports as was described by Guo, Z. et al., Nucleic Acids Research 22:5456 (1994), incorporated herein by reference. Each oligonucleotide probe possessed a fifteen base long dT spacer at its 5' end and a fifteen base long hybridization sequence, as was described by Guo, supra. The hybridization sequences of the oligonucleotide probes, the target region(s) to which they correspond, and their location on the glass support are shown in Table 2. All bases corresponding to target polymorphisms are bold and underlined. All italicized and underlined bases are replaced by 3-nitropyrrole in the artificial mismatch hybridization experiments.

TABLE 2

| Spot Location | Probe Sequence | Perfect Match to: |
|---|---|---|
| First row, left | 5'-GGTGCGGTACCTGGA-3' (SEQ ID No: 13) | (DRB1*0301) |
| First row, right | 5'-GGTGCGGTCCCTGGA-3' (SEQ ID No: 14) | (DRB1*1101, DRB1*1301) |
| Second row, left | 5'-CCTGATGCCGAGTAC-3' (SEQ ID No: 15) | (DRB1*0301) |
| Second row, right | 5'-CCTGATGAGGAGTAC-3' (SEQ ID No: 16) | (DRB1*1101) |
| Third row, left | 5'-GATACTTCTATAACC-3' (SEQ ID No: 17) | (DRB1*1101) |
| Third row, right | 5'-GATACTTCCATAACC-3' (SEQ ID No: 18) | (DRB1*0301, DRB1*1301) |

HLA-DRB target DNA was amplified from human genomic DNA by PCR using one fluorescently tagged primer and one biotinylated primer. The primers employed were 5'-(F)-CGCCGCTGCACTGTGAAGCTCTC-3' (SEQ ID NO:19) and 5'-biotin-TTCTTGGAGTACTCTACGTCT-3'(SEQ ID NO: 20), where F indicates a fluorescein label. PCR was performed in a Perkin-Elmer Cetus Thermocycler Model 9600 using 35 cycles of 94° C. for 30 seconds, 55° C. for 1 minute and 70° C. for 1 minute 30 seconds. This method is described in more detail in Baxter-Lowe, et al., J. Clinical Investigation 84:613–18 (1989), which is incorporated herein by reference.

The two complementary strands were separated, and the fluorescently-tagged strand was hybridized to the support-bound oligonucleotide array. For conventional hybridization, hybridizations were performed at room temperature in 5x SSPE, 0.5% SDS buffer, followed by two 15-minute washing steps at 30° C. using 2x SSPE, 0.1% SDS buffer. The same conditions were used for artificial mismatch hybridization, except a short five minute washing step was performed at room temperature. It is noted that the room temperature washing step was adequate to destabilize duplexes between the probe and the variant targets. Lower melting temperatures are sometimes observed in surface, rather than solution, hybridization reactions, especially with large targets such as PCR fragments. In addition, lower salt conditions were used in this example than were used in the melting temperature analyses presented above, thus further reducing duplex melting temperatures.

Figure 6:
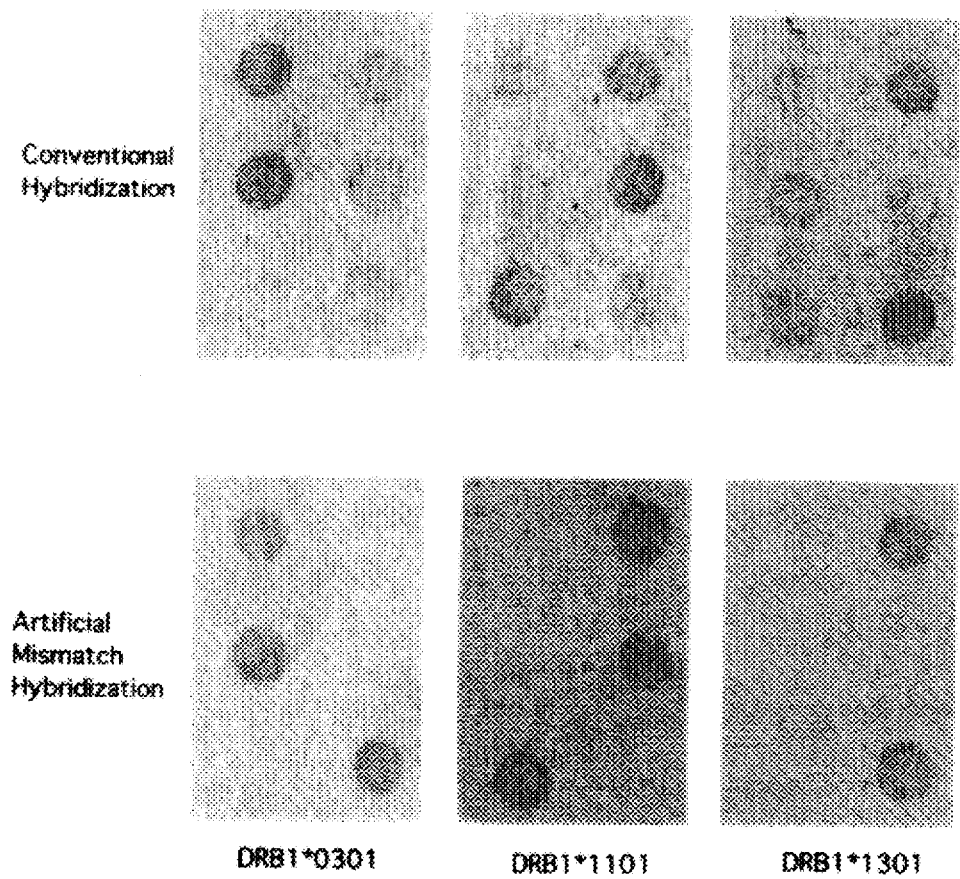
FIG. 6 compares a conventional hybridization method to the artificial mismatch hybridization method of the present invention in an assay for discriminating among closely related alleles of the human HLA-DRB locus.

The hybridization was detected by fluorescence scanning. Fluorescence images were obtained using a Molecular Dynamics FluorImager 575. It is quite clear from FIG. 6 that a fluorescent PCR amplification product yields detectable binding to a perfectly matched probe when the artificial mismatch hybridization method is employed. The method completely discriminates against one or two base mismatch duplexes. In contrast, even after extensive washing, both perfectly matched and mismatched duplexes showed fluorescence signal after the conventional mismatch hybridization method. These results demonstrate the higher discrimination power of the artificial mismatch hybridization approach over the conventional hybridization approach.

The present invention is not intended to be limited to the embodiments disclosed in the Specification or in the Example, but rather to encompass all such modifications and variations of the invention as come within the scope of the following claims.

We claim:

1. A process for hybridizing an oligonucleotide to a first nucleic acid target, the method comprising the steps of:

provinding an oligonucleotide having a nucleic acid sequence complementary in part to the first target, but comprising at least one artificial mismatch relative to the first target and having a nucleic acid sequence complementary in part to a second target, but comprising at least one artificial mismatch and a true mismatch relative to the second target; and combining the oligonucleotide and the first target under selected hybridization conditions to form a first duplex, wherein the first duplex has a melting temperature 1 to 25 C.° higher than that of a second duplex that would form under the same hybridization conditions between the oligonucleotide and a second nucleic acid target, where the oligonucleotide also comprises a true mismatch relative to the second target and where the true mismatch and the artificial mismatch are separated from one another by three or four nucleotide positions and where the artificial mismatch has base stacking properties of a natural nucleoside.

2. A process as claimed in claim 1 wherein the oligonucleotide comprises two artificial mismatches relative to the first and second targets, the artificial mismatches being separated from one another by eight to twelve nucleotides.

3. A process as claimed in claim 1 wherein the oligonucleotide comprises two artificial mismatches separated by ten nucleotides.

4. A process as claimed in claim 1 wherein the artificial mismatch nucleoside is 1-(2'-Deoxy-β-D-ribofuranosyl)-3-nitropyrrole.

5. A process for discriminating between a first nucleic acid target and a second nucleic acid target in a test sample wherein the second nucleic acid target has a sequence variation relative to the first target, the process comprising the steps of:

providing an oligonucleotide having a nucleic acid sequence complementary in part to the first target, including at the position of the sequence variation, but comprising an artificial mismatch relative to the targets at a position other than that of the sequence variation, the artificial mismatch and the sequence variation positions being separated from one another on the oligonucleotide by three or four nucleotide positions, the artificial mismatch having base stacking properties of a natural nucleoside;

combining the oligonucleotide and the test sample under selected hybridization conditions to form a product, the product being selected from the group consisting of (a) a first duplex comprising the oligonucleotide and the first target, (b) a second duplex comprising the oligonucleotide and the second target and being less stable than the first duplex, and (c) a mixture comprising both the first duplex and the second duplex, wherein the first duplex has a melting temperature 1 to 25 C.° higher than that of the second duplex;

selectively detecting the first duplex comprising the oligonucleotide and the first target or the second duplex comprising the oligonucleotide and the second target.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:1:

CAGATCGGCT GAACTCCACA                         2 0

( 2 ) INFORMATION FOR SEQ ID NO:2:

( i ) SEQUENCE CHARACTERISTICS:
　　　　( A ) LENGTH: 20 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:2:

GTCTAGCCGA CTTGAGGTGT　　　　　　　　　　　　　　　　　　　　　　　　　20

( 2 ) INFORMATION FOR SEQ ID NO:3:

( i ) SEQUENCE CHARACTERISTICS:
　　　　( A ) LENGTH: 21 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:3:

AGATACTTCT ATAACCAAGA G　　　　　　　　　　　　　　　　　　　　　　　21

( 2 ) INFORMATION FOR SEQ ID NO:4:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:4:

TGGTTATAGA AGTAT　　　　　　　　　　　　　　　　　　　　　　　　　　　15

( 2 ) INFORMATION FOR SEQ ID NO:5:

( i ) SEQUENCE CHARACTERISTICS:
　　　　( A ) LENGTH: 21 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:5:

GAGAACCAAT ATCTTCATAG A　　　　　　　　　　　　　　　　　　　　　　　21

( 2 ) INFORMATION FOR SEQ ID NO:6:

( i ) SEQUENCE CHARACTERISTICS:
　　　　( A ) LENGTH: 21 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( i x ) FEATURE:
　　　　( A ) NAME/KEY: modified_base
　　　　( B ) LOCATION: group(8, 14)

( i x ) FEATURE:

( A ) NAME/KEY: modified_base
                    ( B ) LOCATION: group(7, 15)

( i x ) FEATURE:
                    ( A ) NAME/KEY: modified_base
                    ( B ) LOCATION: group(6, 16)

( i x ) FEATURE:
                    ( A ) NAME/KEY: modified_base
                    ( B ) LOCATION: group(5, 17)

( i x ) FEATURE:
                    ( A ) NAME/KEY: modified_base
                    ( B ) LOCATION: group(4, 18)

( x i ) SEQUENCE DESCRIPTION: SEQ ID NO:6:

CTCTTGAGAG AGCTAGTATC T                                                          21

( 2 ) INFORMATION FOR SEQ ID NO:7:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: other nucleic acid
                    ( A ) DESCRIPTION: /desc = "oligonucleotide"

( x i ) SEQUENCE DESCRIPTION: SEQ ID NO:7:

GAGAACTCTC TCGATCATAG A                                                          21

( 2 ) INFORMATION FOR SEQ ID NO:8:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: other nucleic acid
                    ( A ) DESCRIPTION: /desc = "oligonucleotide"

( i x ) FEATURE:
                    ( A ) NAME/KEY: modified_base
                    ( B ) LOCATION: group(7, 15)

( i x ) FEATURE:
                    ( A ) NAME/KEY: modified_base
                    ( B ) LOCATION: group(6, 16)

( i x ) FEATURE:
                    ( A ) NAME/KEY: modified_base
                    ( B ) LOCATION: group(5, 17)

( x i ) SEQUENCE DESCRIPTION: SEQ ID NO:8:

CTCTTGAGAG AGCTAGTATC T                                                          21

( 2 ) INFORMATION FOR SEQ ID NO:9:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: other nucleic acid
                    ( A ) DESCRIPTION: /desc = "oligonucleotide"

( x i ) SEQUENCE DESCRIPTION: SEQ ID NO:9:

AGATACTAGC GCTCTCAAGA G                                                          21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:10:

AGATACTAGC TCGCTCAAGA G                    21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:11:

AGATACTAGC GCTCTCAAGA G                    21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:12:

AGATACTAGC TCTCTCAAGA G                    21

( 2 ) INFORMATION FOR SEQ ID NO:13:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:13:

GGTGCGGTAC CTGGA                          15

( 2 ) INFORMATION FOR SEQ ID NO:14:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:14:

GGTGCGGTCC CTGGA                          15

( 2 ) INFORMATION FOR SEQ ID NO:15:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:15:

CCTGATGCCG AGTAC　　　　15

( 2 ) INFORMATION FOR SEQ ID NO:16:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:16:

CCTGATGAGG AGTAC　　　　15

( 2 ) INFORMATION FOR SEQ ID NO:17:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:17:

GATACTTCTA TAACC　　　　15

( 2 ) INFORMATION FOR SEQ ID NO:18:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:18:

GATACTTCCA TAACC　　　　15

( 2 ) INFORMATION FOR SEQ ID NO:19:

( i ) SEQUENCE CHARACTERISTICS:
　　　　( A ) LENGTH: 23 base pairs
　　　　( B ) TYPE: nucleic acid
　　　　( C ) STRANDEDNESS: single
　　　　( D ) TOPOLOGY: linear ( i i ) MOLECULE TYPE: other nucleic acid
　　　　( A ) DESCRIPTION: /desc = "oligonucleotide"

( x i ) SEQUENCE DESCRIPTION: SEQ ID NO:19:

CGCCGCTGCA CTGTGAAGCT CTC　　　　23

```
( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:20:

TTCTTGGAGT ACTCTACGTC T                                      21
```